(12) United States Patent
Sumanaweera et al.

(10) Patent No.: US 6,443,894 B1
(45) Date of Patent: Sep. 3, 2002

(54) MEDICAL DIAGNOSTIC ULTRASOUND SYSTEM AND METHOD FOR MAPPING SURFACE DATA FOR THREE DIMENSIONAL IMAGING

(75) Inventors: Thilaka S. Sumanaweera, San Jose; John I. Jackson, Menlo Park, both of CA (US); Michael G. Curley, Cambridge, MA (US); Randall Schlesinger, San Mateo, CA (US); John A. Hossack, Palo Alto, CA (US); Linyong Pang, Stanford, CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/408,302

(22) Filed: Sep. 29, 1999

(51) Int. Cl.$^7$ ................................................ A61B 8/00
(52) U.S. Cl. ........................ 600/443; 600/441; 128/916
(58) Field of Search ................................ 600/437, 440, 600/441, 443, 447, 407, 439, 445, 453, 454, 455; 128/916; 345/429, 430, 431, 501, 425, 7, 9, 419, 421

(56) References Cited

U.S. PATENT DOCUMENTS

| | | | |
|---|---|---|---|
| 5,282,471 A | * | 2/1994 | Sato ............................. 600/443 |
| 5,285,788 A | * | 2/1994 | Arenson et al. ............. 600/441 |
| 5,497,776 A | * | 3/1996 | Yamazaki et al. ........... 600/445 |
| 5,526,812 A | * | 6/1996 | Dumoulin et al. .......... 600/407 |
| 5,655,535 A | | 8/1997 | Friemel et al. |
| 5,720,291 A | | 2/1998 | Schwartz |
| 5,797,849 A | | 8/1998 | Vesely et al. |
| 5,806,521 A | * | 9/1998 | Morimoto et al. .......... 600/447 |
| 5,817,022 A | * | 10/1998 | Vesely ......................... 600/443 |
| 5,860,924 A | | 1/1999 | Quistgaard |
| 5,899,861 A | | 5/1999 | Friemel et al. |
| 5,916,168 A | * | 6/1999 | Pedersen et al. ............ 600/443 |
| 5,920,319 A | | 7/1999 | Vining et al. |
| 5,928,151 A | | 7/1999 | Hossack et al. |
| 5,986,662 A | * | 11/1999 | Argiro et al. ................ 345/419 |
| 5,995,108 A | * | 11/1999 | Isobe et al. .................. 345/421 |
| 6,004,269 A | * | 12/1999 | Crowley et al. ............ 600/439 |
| 6,139,499 A | * | 10/2000 | Wilk ........................... 600/443 |
| 6,283,918 B1 | * | 9/2001 | Kanda et al. ................ 128/916 |

OTHER PUBLICATIONS

Lorensen, William E.; Jul. 1987; "Marching Cubes: A High Resolution 3D Surface Construction Algorithm" General Electric Company Corporate Research and Development; vol. 21, No. 4; pp. 163–169.

Esther L. Yuh et al.; May 1999; "Computers in Radiology, Virtual Endoscopy Using Perspective Volume–Rendered Three–Dimensional Sonographic Data: Technique and Clinical Applications" pp. 1193–1197.

Jean–Daniel Boissonnat; Mar. 29, 1988; "Shape Reconstruction from Planar Cross Sections"; Computer Vision, Graphics and Image Processing, 44; pp. 1–29.

* cited by examiner

Primary Examiner—Marvin M. Lateef
Assistant Examiner—Ali M. Imam

(57) ABSTRACT

A method and system for mapping surface data onto a geometrical representation of a structure for 3D imaging is provided. A boundary of a structure is determined from one type of data, such as Doppler energy data. Another type of data, such as B-mode data, representing the boundary or an area adjacent the boundary is extracted or identified. The B-mode data is then rendered as a function of the boundary, such as by texture mapping the B-mode data onto or adjacent the boundary. As the user examines the structure representation, the texture mapped data may provide texture details based on an optimally determined representation. The boundary may alternatively be used to select data for volume rendering.

54 Claims, 4 Drawing Sheets

MEDICAL DIAGNOSTIC ULTRASOUND SYSTEM AND METHOD FOR MAPPING SURFACE DATA FOR THREE DIMENSIONAL IMAGING

BACKGROUND

This invention relates to a medical diagnostic ultrasound system and method for three dimensional (3D) imaging. In particular, an image of structure in a body is rendered from data representing three dimensions.

For 3D ultrasound imaging, ultrasound data representing a volume within the body is collected. The ultrasound data comprises B-mode or Doppler mode data. For example, color Doppler data is collected in a series of frames of data representing two dimensional (2D) areas of the body. The frames of data are registered relative to other frames of data. The image is surface or volume rendered from the data registered to represent the volume.

One technique for rendering provides for virtual endoscopy. In virtual endoscopy, color Doppler images represent the point of view of the user as if moving through a structure within the body. The user may better appreciate the internal structure of vessels or better identify areas of stenosis. However, color Doppler data has poor spatial resolution, so little detail about the texture of the structure is provided. Furthermore, the lighting model used is typically chosen arbitrarily. As a result, the displayed structural representation shows the geometry but provides poor textural representation. For example, some plaque may not be visible or represented in the images.

BRIEF SUMMARY

The present invention is defined by the following claims, and nothing in this section should be taken as a limitation on those claims. By way of introduction, the preferred embodiment described below includes a method and system for mapping surface data onto a geometrical representation of a structure for 3D imaging. A boundary of a structure is determined from one type of data, such as Doppler energy data. Another type of data, such as B-mode data, representing the boundary or a volume adjacent the boundary is extracted or identified. The B-mode data is then rendered as a function of the boundary, such as by texture mapping the B-mode data onto or adjacent the boundary. As the user examines the structure representation, the texture mapped data may provide texture details based on an optimally determined representation.

In a first aspect, a medical diagnostic ultrasound method for mapping data for three-dimensional imaging is provided. A boundary is determined from a set of a first type of data representing a three dimensional region. An image is rendered from a set of a second type of data representing the three-dimensional region as a function of the boundary. A system for performing this aspect includes boundary and 3D image processors.

In a second aspect, a medical diagnostic ultrasound method for mapping data for three-dimensional imaging is provided. A boundary is determined from a set of Doppler data representing a three dimensional region. Data from a set of B-mode data representing the three-dimensional region is texture mapped onto the boundary. An image is rendered as a function of the texture mapping.

Further aspects and advantages of the invention are discussed below in conjunction with the preferred embodiments.

DETAILED DESCRIPTION OF THE PREFERRED EMBODIMENTS

For virtual endoscopy or other 3D imaging, two different types of data are used to provide the user with more diagnostic information. A geometric boundary is determined from one type of data, such as ultrasound Doppler energy data. The texture associated with the boundary or a volume adjacent the boundary is determined from a different type of data, such as B-mode data. Each of the two different types of data are selected or optimized for their contribution to the rendered images, such as selecting different data for each of boundary detection and spatial texture mapping.

Data Acquisition

Figure 1:
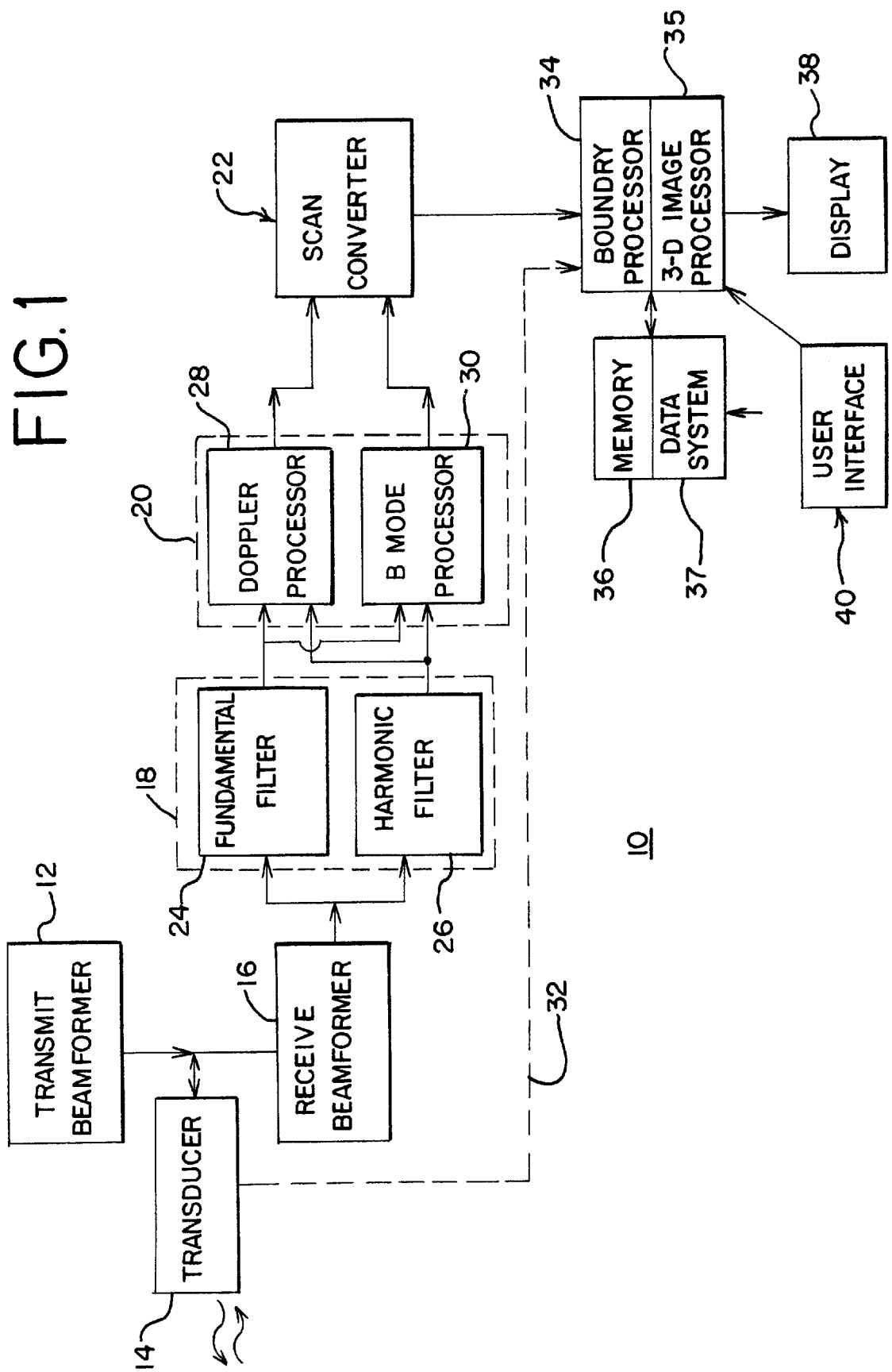
FIG. 1 is a block diagram of one preferred embodiment of a medical diagnostic ultrasound system for 3D imaging.

Referring now to the figures, and in particular, FIG. 1, an ultrasound system is generally shown at 10. The ultrasound system 10 includes a transmit beamformer 12, a transducer 14, a receive beamformer 16, a filter block 18, a signal processor 20 and a scan converter 22. The ultrasound system 10 is configurable to acquire information corresponding to a plurality of two-dimensional representations or image planes of a subject for three-dimensional reconstruction. Other methods, such as those associated with a two dimensional or single element transducer array, may be used. To generate each of the plurality of two-dimensional representations of the subject during an imaging session, the ultrasound system 10 is configured to transmit, receive and process a plurality of transmit events. Each transmit event corresponds to firing an ultrasound scan line into the subject.

The transmit beamformer 12 is a digital or analog beamformer capable of generating signals at different frequencies. In one embodiment, the transmit beamformer comprises the beamformer described in Cole et al., U.S. Pat. No. 5,675,554, assigned to the assignee of the present invention, the disclosure of which is incorporated herein by reference. In this embodiment, once the desired output is defined in terms of very low harmonic signal or any other characteristic, then the ideal output signal is defined in the frequency domain and converted to the time domain. This time domain signal is divided by the carrier to obtain the desired envelope using complex shapes for both the time domain signal and the carrier. This combination of envelope and carrier is programmed into the transmit waveformer. The envelope is sampled at a relatively low frequency, and as a result of imperfections in real implementations, remnants of harmonics relating to the sampling frequency of the carrier and the base band signal may appear in the final result. An additional low pass filter may be used to suppress these remnants.

The transmit beamformer 12 generates one or more excitation signals. Each excitation signal has an associated center frequency. Preferably, the center frequency of the excitation signals is within the 1 to 15 MHz range, such as 2 MHz, and accounts for the frequency response of the transducer 14. The excitation signals preferably have non-zero bandwidth.

The excitation signals from the transmit beamformer 12 are provided to the transducer 14. The transducer 14 is of any construction for converting electrical energy to acoustic energy, such as the one-dimensional, multiple element arrays (e.g. the Acuson 3V2c transducer). 2D arrays, sparse 2D arrays, spiral 2D arrays [See U.S. Pat. 5,808,962], 1.5D arrays and single element transducers may be used. In one embodiment, the transducer comprises multiple arrays, either in parallel or at non-zero angles with respect to each other as disclosed in U.S. application Ser. No. 08/916,585, filed Aug. 22, 1997, the disclosure of which is incorporated herein by reference. In this embodiment, one array may be used for tracking motion of the other imaging array.

The transducer 14 is designed for use external or internal to the body. For example, the transducer is mounted on a catheter (see U.S. Pat. No. 5,876,345, or U.S. Pat. No. 5,699,805 assigned to the assignee of the present invention, the disclosures of which are incorporated herein by reference), a transesophgeal device (see U.S. Pat. No. 6,045,508, filed Feb. 27, 1997, assigned to the assignee of the present invention, the disclosure of which is incorporated herein by reference), an endocavity device, a hand held casing or a surface mounted device.

One or more of the elements in the transducer 14 are excited by an excitation signal to produce ultrasonic acoustic waveforms. In particular, the transducer 14 converts these excitation signals into ultrasonic energy that is directed along transmit beams into the subject, such as the body of a patient. Scattering sites within the subject, such as contrast agents or tissue in the subject, cause echo information to be returned to the transducer 14. This echo information is converted by the transducer 14 into electrical signals that are applied to the receive beamformer 16.

The receive beamformer 16 is of a construction known in the art, such as an analog or digital receive beamformer capable of processing signals associated with different frequencies. The receive beamformer 16 and the transmit beamformer 12 may comprise a single device. In one embodiment, the receive beamformer 16 comprises the beamformer disclosed by Wright, et al. in U.S. Pat. No. 5,685,308, assigned to the assignee of the present invention and incorporated herein by reference. The receive beamformer 16 is preferably programmable.

As known in the art, the receive beamformer 16 delays, apodizes and sums each electrical signal with other electrical signals. An ongoing stream of summed signals represents the ultrasound beam or line, or portions of the lines when multiple transmit focus depths per line are used, received from the body. The receive beamformer 16 generates in phase and quadrature (I and Q) information along one or more scan lines. Alternatively, real value signals may be generated. A complete frame of I and Q information corresponding to a two-dimensional representation (a plurality of scan lines) is preferably acquired before I and Q information for the next frame is acquired.

For imaging pulsatile targets within the subject (e.g. heart or carotid), gating is preferably used to trigger application of the excitation signals to the transducer 14. In order to further improve three-dimensional imaging, only images corresponding to selected portions of the ECG cycle, the breathing cycle or both are utilized. With ECG gating, a window is selected a fixed time duration after the ECG pulse maximum. With breathing cycle gating, it is often simplest to ask the patient to hold his or her breath for the short duration of the ultrasonic scan. Alternatively, chest motion can be recorded using a displacement sensor, and data can be selected for a portion of the breathing cycle. As yet another alternative, the temperature of air in the patient's nostrils is detected.

The receive beamformer 16 passes the signals to the filter block 18. The filter block 18 comprises a processor, digital signal processor, ASIC, dedicated hardware or other filters, including one or both of programmable and non-programmable filters. The filter block 18 passes information associated with a desired frequency band, such as the fundamental band using fundamental band filter 24 or a harmonic frequency band using the harmonic band filter 26. The filter block 18 may be included as part of the receive beamformer 16.

As used herein, harmonic includes sub-harmonics (e.g. ½ of the fundamental), fractional harmonics (e.g. 3/2 of the fundamental) as well as second, third, fourth, and other higher harmonics. The harmonic frequency band preferably does not but may overlap the fundamental frequency band.

In tissue harmonic imaging, no additional contrast agent is added to the target, and only the nonlinear characteristics of the tissue are relied on to create the ultrasonic image. Medical ultrasound imaging is typically conducted in a discrete imaging session for a given subject at a given time. For example, an imaging session can be limited to an ultrasound patient examination of a specific tissue of interest over a period of ¼ to 1 hour, though other durations are possible. In this case, no additional contrast agent is introduced into the tissue at any time during the imaging session.

The harmonic imaging technique described above can be used for both tissue and contrast agent harmonic imaging. In contrast agent harmonic imaging, any one of a number of ultrasound contrast agents is added to the target or subject in order to enhance the non-linear response of the tissue or fluid. The contrast agents radiate ultrasonic energy at harmonics of an insonifying energy at fundamental frequencies.

The fundamental band filter 24 and the harmonic band filter 26 preferably comprise one filter that is programmable to pass different frequency bands, such as the fundamental, second or third harmonic bands. For example, the filter block 18 demodulates the summed signals to baseband. The demodulation frequency is selected in response to the fundamental center frequency or another frequency, such as a second harmonic center frequency. For example, the transmitted ultrasonic waveforms are transmitted at a 2 MHz center frequency. The summed signals are then demodulated to baseband by shifting by either the fundamental 2 MHz or the second harmonic 4 MHz center frequencies (the demodulation frequency). Other center frequencies may be used. Signals associated with frequencies other than near baseband are removed by low pass filtering. As an alternative or in addition to demodulation, the filter block 18 provides band pass filtering. The signals are demodulated to an intermediate frequency (IF)( e.g. 2 MHz) or not demodulated and a band pass filter is used. Thus, signals associated with frequencies other than a range of frequencies centered around the desired frequency or an intermediate frequency (IF) are filtered from the summed signals. The demodulated or filtered signal is passed to the signal processor 20 as the complex I and Q signal, but other types of signals, such as real value signals, may be passed.

The signal processor 20 comprises one or more processors, digital signal processors, ASICs, dedicated hardware or other devices for generating Doppler or B-mode information. Preferably, the signal processor 20 comprises a Doppler processor 28 and a B-mode processor 30. Each of these processors detects information from the received signals. The Doppler processor 28 estimates velocity, variance of velocity and energy from the I and Q signals. The B-mode processor 30 generates information representing the intensity (e.g. envelope, amplitude or power) of the echo signal associated with the I and Q signals. B-mode data, color Doppler velocity data (CDV), color Doppler energy data (CDE), Doppler Tissue data (DTI), Color Doppler Variance data, or combinations thereof are detected.

The information generated by the signal processor 20 is provided to the scan converter 22. Alternatively, the scan converter 22 includes detection steps as known in the art and described in U.S. Pat. No. 5,793,701, assigned to the assignee of the present invention. The scan converter 22 comprises processors, digital signal processors, ASICs and/or dedicated hardware for arranging the output of the signal processor 20 into two-dimensional or three-dimensional representations or frames of image data. Preferably, the scan converter 22 outputs formatted video image data frames, such as DICOM Medical industry image standard format or a TIFF format. Thus, the plurality of two-dimensional representations or a single three-dimensional representation is generated. Each of the representations corresponds to a receive center frequency, such as a second harmonic center frequency, a type of imaging, such as B-mode, and positional information as discussed below.

In one embodiment, separate frames of data for B-mode and Doppler mode data are acquired. For example, the transmission and processing for acquiring each type of data is interleaved as known in the art.

Other types of ultrasound data may be acquired. For example, data representing perfusion of contrast agents into a region of interest is acquired, such as disclosed in U.S. application Ser. No. 09/144,843, filed Aug. 31, 1998, the disclosure of which is incorporated herein by reference. The perfusion data is derived from an absolute measure (e.g. measuring the concentration of contrast agents), a wash-in curve, a wash-out curve, a pulse repetition frequency, other perfusion measurements or combinations thereof. Other measures, including non-ultrasound measurements, of perfusion may be used.

Likewise, tissue viability data may be acquired. Tissue viability ultrasound data preferably comprises data derived as a function of perfusion data and tissue motion data. A measurement of the distance of wall movement may be derived from ultrasound data, such as from Doppler tissue motion data. Alternatively, a boundary is defined and tracked to measure the amount of tissue motion. Other measures, including non-ultrasound measurements, of tissue viability may be used.

The contractility of the heart may be measured. For example, contractility is measured as a function of the change in the heart wall thickness during a cardiac cycle. The wall thickness may be derived from B-mode or Doppler data. An ultrasonic contrast agent may also be used to improve detection of wall boundaries. The contraction information is thus acquired, such as for showing ischemic areas.

In addition or as an alternative to the ultrasound data described herein, other types of data may be acquired by the data system 37. The data system 37 comprises a processor, digital signal processor, ASIC, dedicated hardware, other devices and combinations thereof with a sensor for acquiring one or more of different types of data. For example, the data system 37 comprises a CT scan, MRI, x-ray or optical system. In one embodiment, the electric potential of the heart is mapped, such as with localized electrodes or with a catheter designed to measure the electrical potential on the surface of the cardiac chambers. Either the amplitude or the relative timing as a function of a reference point (e.g. the time a potential is measured relative to the electrical activation of the sino-atrial node in the right atrium of the electrical potential is measured). Likewise, the contractility of the heart is measured either independently of or as a function of the electric potential. The data system 37 may comprise components for measuring the stress, pressure, strain, perfusion, viability, wall motion or other parameters of a body.

The data, whether ultrasound data or other data, is aligned within a representative volume as a function of position information. Many approaches can be taken in aligning the data frames to provide a desired three-dimensional reconstruction. Many of the approaches provide position information associated with the orientation of one data frame relative to other data frames.

Frames of ultrasound data are preferably aligned as a function of acquisition with a same transducer 14. The position information, such as from a rotatable transducer, is provided from the transducer 14 on a line 32. The position information comprises three components of position (X, Y, Z) and three components of rotation (about X, Y, and Z). Other definitions of position and orientation may be used, such as 2 known points and one origin point on each plane.

Three methods for acquiring data representing known locations are described below, though other methods may be used. First, a single element transducer (or an axially focused annular array) is mechanically scanned so as to sweep a volume or three-dimensional space. An example of this first method is the method practiced for the Medison-Kretz Combison 530 (Korea). Moving parts for sweeping the volume are enclosed in a fluid filled housing. Thus, the three-dimensional space is swept by mechanically moving the transducer over two-dimensions.

The second method is to use a two-dimensional, sparse two-dimensional, spiral two-dimensional or 1.5 dimensional transducer array to obtain information directly. A sparse two-dimensional, spiral two-dimensional array can be used to scan electronically in any desired orientation to acquire the desired information. Typically, the sparse two-dimensional array is sub-sampled. It is generally impractical to provide a fully sampled 2D array (e.g. 64×64 is 4096 elements). An example of a sparse two-dimensional array is disclosed in U.S. Pat. No. 5,329,496 (Smith). An imaging system for use with the disclosed array is described in U.S. Pat. No. 5,546,807 (Oxaal et al.). Other subsampled two-dimensional arrays include spiral 2D arrays, such as disclosed in U.S. Pat. No. 5,808,962.

The third method is to collect multiple two-dimensional image data frames associated with relative positional information using a one-dimensional transducer array. The two-dimensional data frames or image planes are non-coplanar, such as two or more rotationally offset planes or two or more planes offset in an elevational position. One dimension is electronically scanned and another dimension is mechanically scanned by rotation, translation, or any combination thereof. For example, the transducer is swept. Sweeping corresponds to rotating the transducer about an axis along the azimuth of the lens surface. The positional information provides the relative position among the data frames so that these frames may be subsequently assembled to form the desired three-dimensional reconstruction.

One approach for this third method is to use manual motion detection techniques based on analysis of ultrasonic images. See Tamura et al., "Three-Dimensional Reconstruction of Echocardiograms Based on Orthogonal Sections" (Pattern Recognition, 18, 2, pp. 115–124, 1985).

Another approach is to sense position based on image motion detection, such as disclosed in MULTIPLE ULTRASOUND IMAGE REGISTRATION SYSTEM, METHOD AND TRANSDUCER, U.S. application Ser. No. 08/621,561, filed Mar. 25, 1996, U.S. application Ser. No. 08/807,498, filed Feb. 27, 1997 and U.S. application Ser. No. 08/916,585, filed Aug. 22, 1997 to Hossack et al., assigned to the assignee of the present invention, and the disclosures of which are herein incorporated by reference. The position information is calculated from scan data as a function of the correlation of data. In alternative embodiments, the rate of speckle de-correlation is measured between frames of data. The rate of speckle de-correlation indicates an amount of movement between the frames of data.

Friemel et al. describes in U.S. Pat. Nos. 5,655,535 and 5,899,861 other approaches to determining the amount of motion between frames of data. For example, the relative time delay between signals from two transducer elements in a 2D array in the near field is directly proportional to transducer velocity. As another example, transducer motion is measured as a function of spectral broadening. As a transducer element is translated, a fast Fourier transform is performed on data received from a given range. The resulting spectrum is a function of the transducer element geometry, the pulse repetition frequency, and the velocity of transducer movement. As yet another example, the power function of an echo signal at a single transducer element is proportion to the elevational velocity. As another example, the spectral peak magnitude is used. Comparisons of the locations of the peak magnitude locations are used to estimate elevation translation or motion. Other techniques disclosed by Friemel et al. may be used.

Schwartz U.S. Pat. No. 5,474,073 describes a qualitative three-dimensional method using a hand-held transducer array and an assumed scan motion. The transducer is moved manually by free hand motion. The spacing between each two-dimensional image is assumed to be equal.

Keller U.S. Pat. No. 5,353,354 discloses a transducer array equipped with accelerometers or magnetic sensors designed to measure the position and orientation of the transducer, and, therefore, relative motion between respective image planes. The free hand movement of the transducer is monitored. Suitable magnetic positioning sensors are described in U.S. Pat. Nos. 4,945,305 and 4,849,692 to Blood. Preferably, a pulsed DC type position sensor is used for this type of transducer. Such systems include the mini Bird™ and Flock of Birds™ systems by Ascension Technology Corp. of Burlington, Vt. This device is less susceptible to interference from ferrous objects. Alternatively, the 3Space Fastrack® from Polhemus (Colchester, Vt.) is used.

In one embodiment, magnetic position sensors are mounted on a catheter. The catheter is inserted into the body. Sensors external to the body determine a position of the catheter and transducer array mounted thereon to register each frame of data relative to another frame of data. The position is determined through triangulation. The position is determined through use of a 6-D (i.e., position and orientation) magnetic position tracker, such as the 3Space Fastrack® manufactured by Polhenus, Inc., Naga manufactured by Biosense or the miniBird™ manufactured by Ascension Technology Corp. For example, the catheter includes a transducer array that is rotated to acquire data representing a toroid volume. The position of the catheter and associated scan planes are determined from the position sensor and angle of rotation.

Mechanical manipulation guides or fixtures capable of rotation, translation, or a fan-like sweep may also be used to spatially orient each two-dimensional image plane. Such devices are disclosed in U.S. Pat. No. 5,454,371 (Fenster) and U.S. Pat. No. 5,562,095 (Downey et al.).

Another approach is to provide a spaced arrangement of LEDs, such as infra-red LEDs, on the transducer. The LEDs are activated in sequence and monitored with a camera. The position and orientation is then inferred from an image of the LEDs generated by the camera. One such device is manufactured by Surgical Navigation Technologies of Broomfield, Colo.

Still another approach is to use a spaced arrangement of microphones. See King U.S. Pat. No. 4,100,916. The position information is determined from the time of flight of acoustic impulses generated by a source on the transducer to the various microphones.

Yet another approach is to use a motorized array to collect the desired set of image data frames by precisely controlling the movement of the transducer array. One example is the Acuson V5M Transesophageal transducer, a rotating transducer. The rotating transducer produces two-dimensional images at known angles of rotation. A lens design for such a transducer is shown in U.S. Pat. No. 5,562,096 (Hossack, et al., assigned to the assignee of the present invention). Another example is a transthoracic transducer, such as disclosed in Pini U.S. Pat. No. 5,159,931. See also, Sapoznikov et al., "Left Ventricular Shape, Wall Thickness and Function Based on Three-Dimensional Reconstruction Echocardiography" ("Computers in Cardiology," IEEE Computer Society Press, Cat CH 2476-0, pp. 495–498, 1987). A related approach is to use a large rotating transducer as described in McCann et al., "Multidimensional Ultrasonic Imaging for Cardiology" (Proceedings of IEEE, 76, 9, pp. 1063–1072, September 1988). For example and preferably for use with harmonic imaging, an Acuson 3V2c transducer is placed in a rotatable fixture, such as disclosed in Pini or McCann.

The frames of different types of ultrasound data are registered or aligned relative to each other by any of the methods described above or other methods. For example, frames of B-mode data are acquired as a function of measured position information and then frames of Doppler data are acquired as a function of the same type of position information. As another example, frames of harmonic B-mode data and fundamental B-mode data are acquired as a function of the same transmissions or type of position information. Preferably, the chances for errors in the registration are reduced by interleaving acquisition of the different types of data. For example, one or more lines or frames of Doppler data are acquired for each line or frame of B-mode data.

Non-ultrasound data, such as electric potential data, is aligned with respect to the coordinate reference of the ultrasound data. For example, a catheter for acquiring ultrasound data and electric potential data may include a position sensor. Other common reference measurements may be used, such as using two different devices with a same type of sensor for measuring position in the same way. In other embodiments, the data is aligned as a function of correlation with other data, such as where both frames of data represent a same structure of the body. Other techniques for aligning non-ultrasound data with other non-ultrasound data or with ultrasound data may be used, whether known or yet developed.

Figure 2:
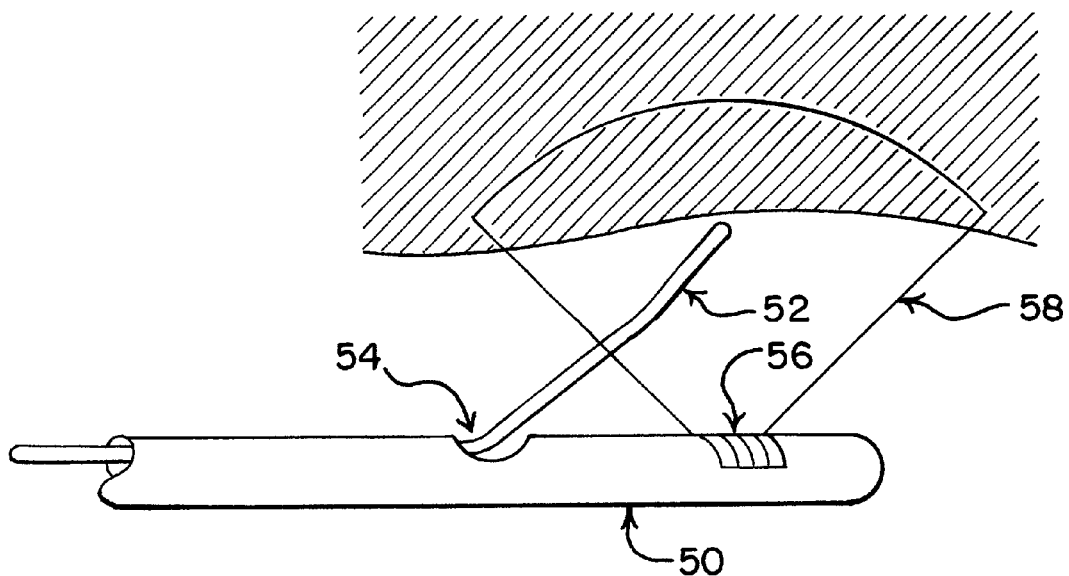
FIG. 2 is side view of a catheter with an ultrasound transducer and a cardiac parameter measurement catheter extension.

FIG. 2 shows one embodiment of a catheter 50 designed to register non-ultrasound frames of data with ultrasound frames of data. A device 52 for measuring electrical potential of the heart wall extends from a port 54 in the catheter 50. A transducer array 56 is positioned so that a portion of the device 52 (e.g. the end of the device 52) is within a scan plane 58 of the transducer array 56. By identifying the location of the device 52 in the ultrasound image, the non-ultrasound data is acquired simultaneously with ultrasound data at known points within the scan plane 58. The position of the catheter 50 for registration of the ultrasound frames of data is determined using any of the techniques discussed above, such as magnetic position sensors. In one embodiment, the catheter comprises one of the catheters disclosed in U.S. Pat. No. 5,325,860, U.S. Pat. No. 5,345,940, U.S. Pat. No. 5,713,363, U.S. Pat. No. 5,704,361 or U.S. Pat. No. 5,699,805. Alternatively, the device 52 is separate from the catheter 50 and the position is determined using any of the techniques discussed above, such as magnetic position sensors. A representation of the device 52, such as a representation of the tip or transducer, may be added to the 3D or 4D rendering. Preferably, a surface rendering is used where a representation is added.

Three Dimensional Rendering

Referring to FIG. 1, the position information and the ultrasound data frames and/or non-ultrasound data frames are provided to a boundary processor 34 and a 3D image processor 35 via a cable or other data link. Preferably, the boundary processor 34 and 3D image processor 35 comprise a single remote computer for real time or delayed reconstruction and rendering. Alternatively, an on-board computer and/or separate processors or computers are used. Preferably, the processors 34 and 35 comprise at least an Intel Pentium PC (400+ MHz) or SGI($O_2$ or Octane for example) with a memory 36. Preferably, the memory 36 is large, such as 128 MB RAM. Image data frames from the scan converter 22 can be compressed using any suitable compression technique such as JPEG prior to transfer. After the image data has been received, it is decompressed. For example, 3D reconstruction is performed on a remote workstation such as the AEGIS workstation of Acuson Corporation, the assignee of the present invention. Thus, the reconstruction and display of a three dimensional representation is either during the imaging session or after the imaging session.

For reconstruction, the boundary processor 34 and 3D image processor 35, with the memory 36, use the image data frames and the position information to generate information for the three dimensional representation. Information from the two-dimensional image data frames is converted to a 3D grid, such as a preferred regularly (equal) spaced volume grid. Equal spacing allows for efficient calculations and use with low cost visualization software. The image data frame for a central plane is inserted at a plane aligned with the center of the volume. Working outwardly from this center plane, successive image data frames are inserted into their appropriate XYZ locations, as a function of the positional information. Once all frames have been inserted, intermediate points are calculated using three-dimensional linear interpolation techniques relying on the eight closest known data points. In one embodiment, the three-dimensional image data provided by the scan converter 22 is already in a 3D grid, avoiding conversion to a 3D grid.

The processors 34 and 35 use software to construct the 3D representation based on the input information discussed above. Various commercially available software and fixtures are available for 3D reconstruction. For example, TomTec GmbH (Unterschleissheim, Germany) offers software and mechanical fixtures specifically for 3D ultrasound. The software is capable of 3D reconstruction based on several different scan formats, such as rotations and freehand scanning. Life Imaging System Inc. (London, Ontario, Canada) also provides software and mechanical scanning fixtures for 3D ultrasound. VayTek Inc. (Fairfield, Iowa) produces rendering software for a 3D volumetric regularly spaced, orthogonal grid data. As yet another example, Advanced Visual Systems Inc. (Waltham, Mass.) offers an AVS5 software package for constructing and rendering 3D representations from the plurality of image data frames.

Alternatively, the software for reconstruction of the 3D representation is written specifically for the system 10 described above. A standard language, such as C or C++, is used with WindowsNT® (Microsoft) and a graphics Applications Programming Interface (e.g. OpenGL® (Silicon Graphics Inc.)). Other languages, programs, and computers may be used.

In alternative embodiments, the frames of data and positional information are not interpolated to the 3D grid. The boundary detection and rendering discussed below are performed as a function of the frames of data and the positional information without reformatting.

Figure 3:
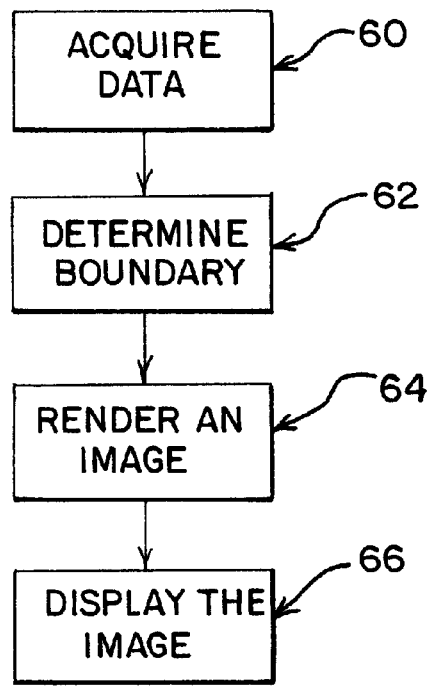
FIG. 3 is a flow chart representing operation of the system of FIG. 1.

The boundary processor 34 and 3D image processor 35 detect a boundary and render an image as a function of the boundary, respectively. Referring to FIG. 3, a flow chart of a method for 3D imaging is shown. In steps 60, data is acquired, such as the frames of ultrasound and/or non-ultrasound data or data in the 3D grid. At least two different types of data are acquired. For virtual endoscopy, the data represents a structure, such as a blood vessel, a heart chamber, an interface between fluid and tissue, an interface between different tissues or other identifiable interfaces.

The boundary processor 34 (FIG. 1) determines a boundary in act 62. For example, a boundary representing a section of a vessel is determined from frames of Doppler energy ultrasound data. One or more of various methods for determining the boundary are used.

In one embodiment, the boundary is determined as a function of a threshold. A threshold is applied to the frames of data or the 3D grid of data. Any locations corresponding to data values transitioning from above to below the threshold value represent the boundary. For example, an enclosed structure, such as a vessel, is imaged in cross-section with Doppler data. A center of gravity of the enclosed structure represented by the frame of data is determined. At various angles from the center of gravity, such as every 10 degrees, the first spatial location where Doppler data is thresholded to a zero value is selected as a boundary point. The boundary points are connected to form the boundary. This process is repeated for each frame of data to identify the boundary in three dimensions.

In another embodiment, the boundary is determined as a function of the maximum gradient. The frames of data or data in the 3D grid is filtered along each dimension. After filtering the data, the derivative between spatial locations is determined. The derivative represents the gradient between adjacent points. The maximum gradient represents the boundary. One such technique is disclosed by Zucker et al. in "A Three Dimensional Edge Operator", IEEE Transactions on Pattern Recognition and Machine Intelligence, Vol. PAMI-3, No.3, May 1981.

In yet another embodiment, a marching cubes technique is used. The data is divided into cubes with data representing each corner of a cube. A boundary plane, if any, is determined through the cube, based on application of a threshold. The boundary planes of the cubes are linked together, providing a three-dimensional boundary. One such technique is described by Lorensen et al. in "Marching Cubes: A High Resolution 3D Surface Reconstruction Algorithm", Computer Graphics, Vol. 21, pp. 163–169, 1987.

In another embodiment, tetrahedral tessellation is used. The 3D space is divided into tetrahedrons. The contours associated with the tetrahedrons representing the boundary are determined using Voronoi triangulation in 3D. One such technique is described by Boissonnat in "Shape Reconstruction from Planar Cross Sections", Computer Vision, Graphics and Image Processing, Vol. 44, pp. 1–29, 1988. Another such technique is described by Watson in "Computer n-dimensional Delaunay Tessellation with Applications to Voronoi Polytopes", The Computer Journal, Vol.24, No. 2, pp. 167–172, 1981.

Another automatic border detection technique used in the presence of ultrasound speckle as applied to the 2D planes is disclosed by H. E. Melton, Jr. and D. J. Skorton in "REAL-TIME AUTOMATIC BOUNDARY DETECTION IN ECHOCARDIOGRAPHY", 1992 Ultrasonics Symposium, p 1113–17.

Other boundary detection techniques may be used. For example, the boundary is defined in response to user input, such as tracing the boundary in various 2D planes. Multiple boundary techniques may also be used. The detected boundaries are then averaged or otherwise combined to define a common boundary. Once the boundaries are determined, a polygon mesh is formed to represent the surface.

An image is then rendered as a function of the boundary in act 64. The image is rendered using a different type of data than the data used for boundary detection. For example, B-mode data representing the same or adjacent locations as the identified boundary is extracted. The extracted B-mode data is perspectively projected to render an image. The image is rendered as a function of the boundary by either texture mapping the data onto the previously determined boundary or by using the boundary as part of the rendering process, such as by using the boundary to define the data selected for volume rendering.

For texture mapping, data representing the boundary is extracted and mapped onto the boundary. For extraction, data representing the same or adjacent spatial locations as the boundary is selected. In one embodiment, B-mode data adjacent to the boundary on a side opposite the center of gravity of an enclosed structure is selected. For example, B-mode data positioned within a range of the boundary and above a threshold is selected. In an alternate embodiment, B-mode data corresponding to a neighborhood of locations near the boundary is first selected. The number representing the weighted sum of these B-mode data is used for texture mapping the boundary.

The extracted data is mapped. Preferably, OpenGL commands are used to texture map the data. For each section or polygon of the geometric boundary, data representing the texture is provided.

Figure 4:
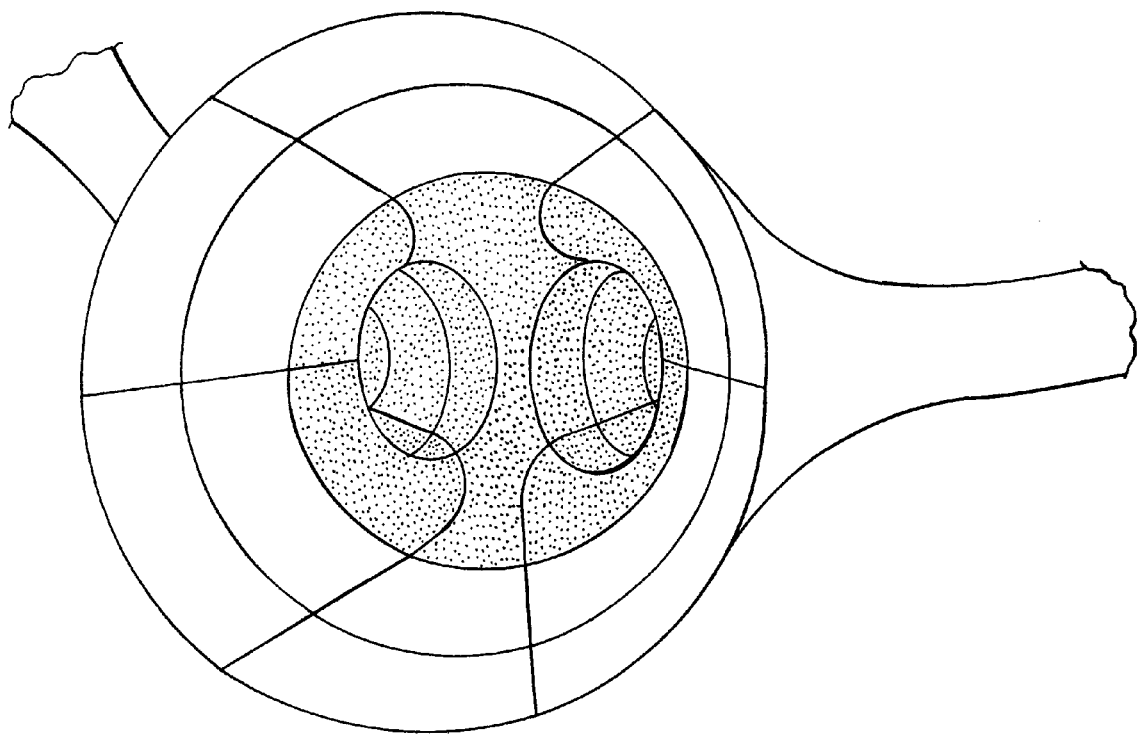
FIG. 4 is a graphical representation of a rendered image.

The mapping includes rendering the image. Preferably, perspective projection rendering is performed, but other surface rendering techniques may be used. As shown in FIG. 4, perspective projection rendering allows the user to visualize the boundary. In FIG. 4, the boundary comprises a vessel. The geometry is shown as well as texture on the geometry. The texture data may be rendered with lighting cues, such as Gouraud or Phong shading. Gouraud shading is generally simpler than Phong shading and may be accelerated with suitable hardware, but Phong shading produces a higher quality image.

The image is regenerated as the user's perspective changes. For example, a sequence of images is provided to simulate moving through the enclosed structure, such as by providing virtual endoscopy. In alternative embodiments, the images represent moving along an outside or non-enclosed surface. The images show both the shape or geometry of the boundary and the texture or other characteristic of the boundary. The other characteristic depends on the type of data used for texture mapping.

Referring to FIG. 1, in one preferred embodiment, the images rendered are responsive to a user interface 40. The user interface 40 comprises a keyboard, trackball, mouse, dedicated keys, software controlled buttons, touch screen or other input devices. The perspective displayed to the user is controlled in response to the user interface 40. The user changes the perspective for rendering by selecting a visual position. Visual positions for rendering are selected to examine the geometry and/or texture of the rendered boundary. For example, the user causes the system 10 to generate a series of images of the carotid artery. The series of images correspond to moving the visual position along a path through the structure. The user causes the moving perspective to stop adjacent to a likely area of stenosis on the boundary. By inspecting the texture of the boundary, plaque or other abnormalities may be detected.

In addition or as an alternative to surface rendering, the 3D image processor 35 volume renders the images as a function of the boundary. The boundary is used to select the data used for volume rendering. For example, data representing spatial locations between two boundaries are used for volume rendering. Any of the techniques discussed above or an arbitrary function may be used to determine the second boundary. For example, the heart walls comprise chamber interfaces and exterior interfaces. Both interfaces are determined as boundaries. In alternative embodiments, only one boundary is determined and data on one side of the boundary is used for volume rendering.

Figure 5:
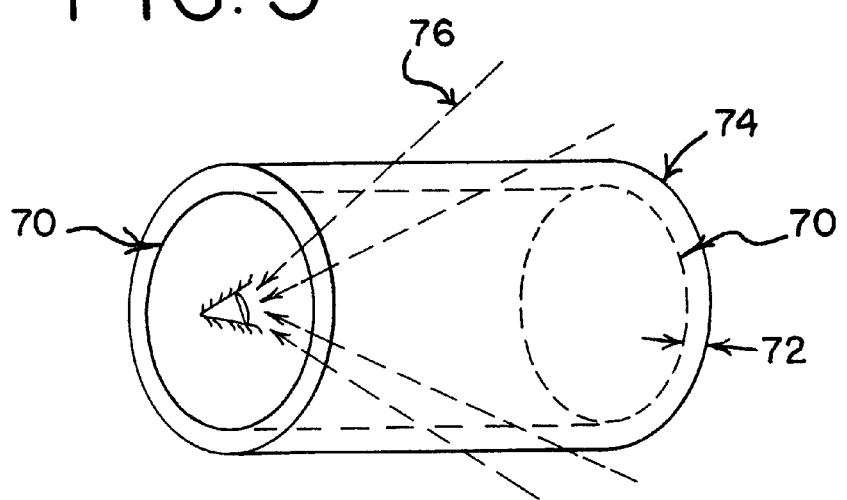
FIG. 5 is a graphical perspective representation of a point of view for 3D rendering.

In one embodiment represented by FIG. 5, a second boundary 74 is determined as a distance 72 from a first boundary 70. The distance 72 is user selected or pre-programmed and may vary as a function of the location or application. Two surfaces are then rendered. Alternatively, the data between a given boundary and some imaginary or arbitrary boundary enclosing or adjacent the given boundary is used for volume rendering.

Once selected, the data is volume rendered in one of various ways, such as alpha bending, maximum intensity or minimum intensity projection. The volume is rendered from a user perspective within an enclosed structure or external to the structure. Based (1) on a range of viewing angles, such as 120 degrees, and the incremental values between each viewing angle, such as 1 degree, or (2) a number of different user perspectives along a 3D trajectory, a number of three dimensional projections is determined. Each projection corresponds to a viewing plane that is perpendicular to the viewing direction that radiates outward. The 3D data samples at each viewing angle are summed along the lines of vision or "into" the 3D grid or viewing plane. Thus, a value for each region in a viewing plane is determined.

For alpha bending, a weighting is applied to each 3D data sample. The weighting values are selected to emphasize near objects. Thus, a sense of front and back regions is created. In an alternate embodiment, the weights correspond to opacity values assigned to each voxel as a function of the data. Alpha bending allows viewing of internal objects relative to surrounding objects. Instead of alpha bending, maximum, minimum or other functions may be used. For maximum or minimum intensity projection, the maximum or minimum 3D data sample, respectively, is used instead of the summation along each line. Other viewing techniques may be used.

Alternative Embodiments

Figure 6:
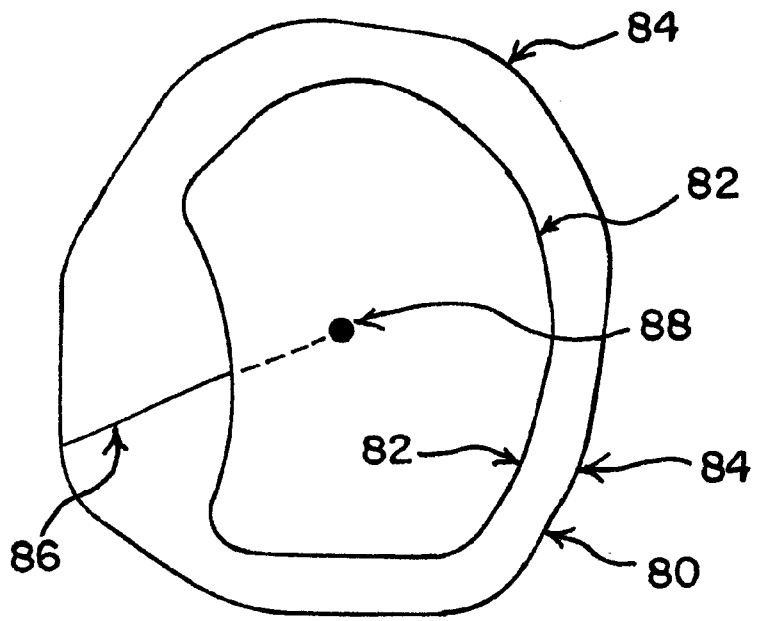
FIG. 6. is a cross-sectional representation of a vessel.

In one embodiment, two boundaries are determined for surface rendering. The two boundaries are used to calculate the data used for texture mapping. For example, vessel wall thickness is texture mapped onto a boundary. See FIG. 6 showing a vessel 80 with first and second boundaries 82 and 84.

To calculate the wall thickness, line segments 86 between the two boundaries 82 and 84 are defined. If the inner boundary 82 corresponds to the inside of a vessel, a line segment 86 is determined from cross-sectional planes of data that are normal to the vessel flow. Within the cross-sectional plane, a centroid or center of mass 88 is determined by:

$$\hat{x} = \frac{\int_S x\, dS}{\int_S dS}, \hat{y} = \frac{\int_S y\, dS}{\int_S dS}$$

where the integral surface is the 2D region enclosed by the surface in the cross section plane. Alternatively, the loci of points on the boundaries are spatially low pass filtered (smoothed) prior to computation of the centroid. For each point along the first or second boundary that is to be used for texture mapping, a line from the centroid 88 through the point and through both boundaries 82 and 84 defines the line segment 86. The distance along the line segment 86 between the two boundaries 82 and 84 is calculated. This distance is mapped onto the boundary during rendering.

The line segment 86 may be defined using other methods. For example, a specific direction, such as down or normal to one of the boundaries, is used to project the lines between the boundaries. As another example, the distance of the line segment 86 is determined as a function of the ray lines used for perspective projection rendering (e.g. line of sight or the distance between two boundaries along a line with an origin at a user point of view).

Figure 7:
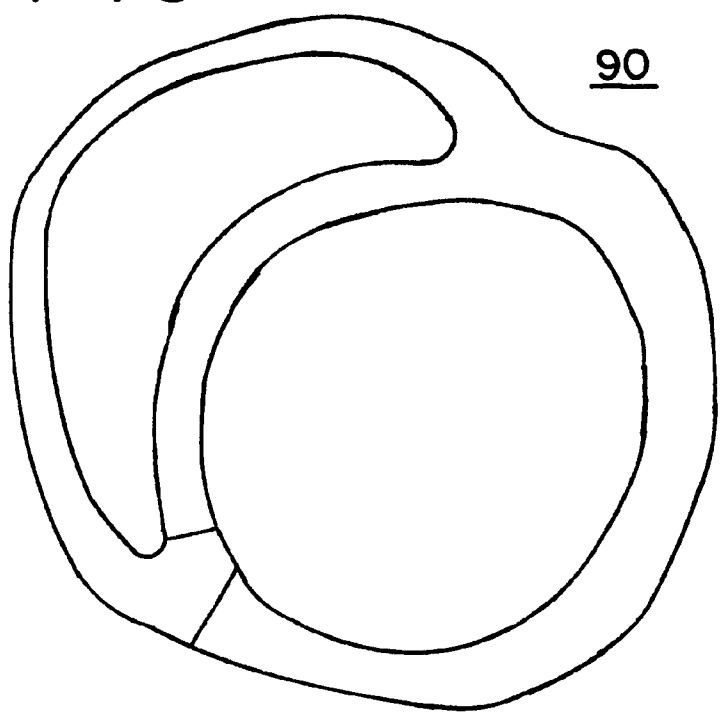
FIG. 7 is a cross-sectional representation of a heart.

As yet another example, the minimum distance to the outer boundary from a point in the inner boundary is used. For imaging the cardiac endocardium (i.e. the inner lining of the heart), a minimum distance definition of the line segment is preferred. FIG. 7 shows a cross-sectional view of a heart 90. An outer boundary of the heart 90 comprises the endocardial boundary of an adjoining cardiac chamber and/or the epicardium (i.e. serous pericardium) on the outside of the heart 90. The minimum distance comprises the thinnest wall thickness measured, rather than the thickness including another chamber. In yet another example, the data between the inner and outer boundaries are processed differently as a function of the distances between the two boundaries. For example, a different color is assigned for different distances. The processed data is used for texture mapping.

In another embodiment, the techniques described herein are used to guide a surgical intervention. An anatomical structure, such as the liver, is ultrasonically scanned. Sets of ultrasound B-mode and Doppler energy data are configured on the same 3D grid. The boundary is determined from the B-mode data. Other types of data may be used for one or both of boundary detection and rendering.

The texture of the surface is determined from the Doppler data. For example, various color information is added as texture. The color varies as a function of the Doppler data at the boundary. In alternative embodiments, the texture color varies as a function of depth from the boundary of Doppler data above a threshold and the amplitude of the Doppler signal. A range of hues indicates the depth of a high amplitude Doppler signal within a distance, such as 4 centimeters. Luminance of the hue indicates the amplitude of the signal. High amplitude Doppler signals nearer the boundary are used instead of signals further from the boundary, or the signals are averaged or weighted and averaged. For areas where the Doppler data below the boundary (i.e. within the anatomical structure) is below the threshold, shades of grey are mapped to the boundary. Other color schemes may be used. A surgeon uses the resulting image to determine where and how deep cuts may be made without reaching a blood vessel.

In other embodiments, images representing four dimensions are rendered where the fourth dimension comprises time. Frames of data from different points in the heart cycle or another cycle are obtained. The images rendered at any given point in time correspond to the appropriate portion of the cycle. The boundary and rendering are performed separately for each time within the cycle. As the user views the images representing the structure, the structure changes as a function of time.

In yet another embodiment, further information is superimposed within the rendered image. For example, the catheter 50 of FIG. 2 is represented graphically on the image. Using the magnetic position sensor or other positioning information as discussed above, the position of the catheter 50 relative to the scanned volume is determined. Based on the size and shape information, the catheter 50 is rendered in the image. The user then knows the position of the catheter prior to ablating tissue or for orienting the catheter 50.

While the invention has been described above by reference to various embodiments, it will be understood that many changes and modifications can be made without departing from the scope of the invention.

It is therefore intended that the foregoing detailed description be understood as an illustration of the presently preferred embodiments of the invention, and not as a definition of the invention. It is only the following claims, including all equivalents, that are intended to define the scope of this invention.

What is claimed is:

1. A medical diagnostic method for mapping data for three-dimensional imaging, the method comprising the acts of:
   (a) determining a boundary from a set of a first type of ultrasound data representing a three dimensional region; and
   (b) rendering an image from a set of a second, different type of ultrasound data representing the three-dimensional region wherein the rendering is performed as a function of the boundary.

2. The method of claim 1 wherein act (a) comprises determining the boundary from Doppler data.

3. The method of claim 2 wherein act (a) comprises determining the boundary from Doppler energy data.

4. The method of claim 3 wherein act (b) comprises rendering from B-mode data.

5. The method of claim 2 wherein act (b) comprises rendering from B-mode data.

6. The method of claim 1 wherein act (b) comprises rendering from B-mode data.

7. The method of claim 6 wherein the B-mode data is harmonic B-mode data.

8. The method of claim 1 wherein act (a) comprises applying a threshold to the set of the first type of ultrasound data.

9. The method of claim 1 wherein act (b) comprises rendering the image from data of the set of the second type of ultrasound data that represents the boundary.

10. The method of claim 1 wherein act (b) comprises surface rendering.

11. The method of claim 1 wherein act (b) comprises rendering selected from the group consisting of: volume rendering and maximum intensity projection rendering.

12. The method of claim 11 wherein act (b) comprises:
(b1) selecting a sub-set of data from the set of the second type of ultrasound data, the sub-set of data being within a region adjacent the boundary;
(b2) volume rendering from the sub-set of data.

13. The method of claim 1 further comprising:
(c) texture mapping the set of the second type of ultrasound data onto the boundary.

14. The method of claim 1 wherein act (b) comprises perspective projection rendering.

15. The method of claim 1 further comprising:
(c) rendering as a function of a user selectable visual position.

16. The method of claim 15 further comprising:
(d) generating a plurality of images as a function of changing position data from a user interface.

17. The method of claim 1 further comprising:
(c) determining a second boundary;
wherein the second type of data comprises a distance between the boundary and the second boundary.

18. The method of claim 17 further comprising:
(d) assigning a color as a function of the distance.

19. The method of claim 1 further comprising:
(c) determining a second boundary;
wherein the second type of data comprises data representing locations between the boundary and the second boundary of the group consisting of: representation of an amount of plaque, an amount of contrast agent, an estimate of tissue perfusion, an estimate to tissue viability, and combinations thereof.

20. The method of claim 1 wherein act (b) comprises rendering from electric potential data.

21. The method of claim 1 wherein at least one of the first and second types of data are acquired from a transducer within a body, the transducer comprising one of the group consisting of: a catheter mounted transducer, a transesophageal transducer and a endocavity transducer.

22. The method of claim 1 further comprising:
(c) aligning the set of the first type of data with the set of the second type of data.

23. The method of claim 22 wherein acts (c) comprises interleaving acquisition of the sets.

24. The method of claim 1 wherein the first type of data comprises one of harmonic and fundamental B-mode data and the second type of data comprises the other of: harmonic and fundamental B-mode data.

25. The method of claim 1 wherein acts (a) comprises determining the boundary from B-mode data.

26. The method of claim 1 further comprising:
(c) representing a portion of a device in the image.

27. The method of claim 1 further comprising:
(c) repeating (b) as a function of time.

28. The method of claim 1 further comprising:
(c) combining data from a neighborhood adjacent the boundary wherein (b) comprises rendering from the second type of data that is responsive to (c).

29. A medical diagnostic ultrasound system for mapping data for three-dimensional imaging, the system comprising:
a boundary processor for determining a boundary from a set of a first type of ultrasound data representing a three dimensional region;
a three-dimensional image processor for rendering an image from a set of a second different type of ultrasound data representing the three-dimensional region as a function of the boundary; and
a display for displaying the image.

30. The system of claim 29 further comprising a Doppler processor wherein the boundary is determined from Doppler data.

31. The system of claim 30 further comprising a B-mode processor wherein the image is rendered from B-mode data.

32. The system of claim 29 further comprising a B-mode processor wherein the image is rendered from B-mode data.

33. The system of claim 29 wherein the boundary processor is operable to apply a threshold to the set of the first type of ultrasound data.

34. The system of claim 29 wherein the three-dimensional image processor is operable to render the image from data of the set of the second type of ultrasound data that is at the boundary.

35. The system of claim 29 wherein three-dimensional image processor is operable to surface render the image.

36. The system of claim 29 wherein the three-dimensional image processor is operable to select a sub-set of data from the set of the second type of ultrasound data, the sub-set of data being within a region adjacent the boundary, and to volume render from the sub-set of data.

37. The system of claim 29 wherein in the three-dimensional image processor is operable to texture map the set of the second type of ultrasound data onto the boundary.

38. The system of claim 29 wherein the image comprises an endoscopic rendering.

39. The system of claim 29 further comprising a user interface, the rendering being a function of a user selectable visual position.

40. The system of claim 29 wherein the boundary processor is operable to determine a second boundary, where the second type of data comprises a distance between the boundary and the second boundary.

41. The system of claim 29 wherein the boundary processor is operable to determine a second boundary, where the second type of data comprises data representing locations between the boundary and the second boundary of the group consisting of: representation of an amount of plaque, an amount of contrast agent, an estimate of tissue perfusion, an estimate to tissue viability, and combinations thereof.

42. The system of claim 29 wherein the three-dimensional image processor is operable to render the image from electric potential data.

43. The system of claim 29 wherein at least one of the first and second types of data are acquired from a transducer within a body, the transducer comprising one of the group consisting of: a catheter mounted transducer, a transesophageal transducer and a endocavity transducer.

44. A medical diagnostic method for mapping data for three-dimensional imaging, the method comprising the acts of:
(a) determining a boundary from a set of Doppler data representing a three dimensional region;
(b) texture mapping data from a set of B-mode data representing the three-dimensional region onto the boundary; and
(c) rendering an image as a function of (b).

45. The method of claim 44 wherein act (c) comprises perspective projection rendering.

46. The method of claim 44 wherein act (a) comprises determining the boundary from Doppler energy data.

47. The method of claim 44 wherein act (a) comprises applying a threshold to the set of Doppler data.

48. The method of claim 44 wherein act (c) comprises surface rendering.

49. The method of claim 44 wherein act (b) comprises selecting data from the set of B-mode data that spatially corresponds to the boundary.

50. The method of claim 44 wherein act (c) comprises perspective projection rendering.

51. The method of claim 50 wherein act (c) comprises rendering as a function of a user selectable visual position.

52. The method of claim 44 wherein at least one of the first and second types of data are acquired from a transducer within a body, the transducer comprising one of the group consisting of: a catheter mounted transducer, a transesophageal transducer and a endocavity transducer.

53. The method of claim 44 further comprising:
(d) aligning the set of Doppler data with the set of B-mode data.

54. The method of claim 53 wherein acts (d) comprises interleaving acquisition of the sets.

* * * * *